US009053616B2

(12) United States Patent
Grabiner et al.

(10) Patent No.: US 9,053,616 B2
(45) Date of Patent: Jun. 9, 2015

(54) COMPUTING SYSTEMS AND METHODS FOR ELECTRONICALLY INDICATING THE ACCEPTABILITY OF A PRODUCT

(75) Inventors: Frederick Robert Grabiner, Livingston, NJ (US); Carl Michael Lentz, Cedar Knolls, NJ (US); Emily Moore, Haddam Neck, CT (US); Thaddeus Prusik, Stroudsburg, PA (US); Nicholas Puro, Briarcliff Manor, NJ (US)

(73) Assignee: TEMPTIME CORPORATION, Morris Plains, NJ (US)

( * ) Notice: Subject to any disclaimer, the term of this patent is extended or adjusted under 35 U.S.C. 154(b) by 580 days.

(21) Appl. No.: 12/799,252

(22) Filed: Apr. 20, 2010

(65) Prior Publication Data

US 2011/0258130 A1    Oct. 20, 2011

(51) Int. Cl.
*G06Q 99/00*    (2006.01)
*G07G 1/00*    (2006.01)
*G06Q 10/08*    (2012.01)
*G06Q 30/00*    (2012.01)

(52) U.S. Cl.
CPC ............ *G07G 1/0081* (2013.01); *G06Q 10/087* (2013.01); *G06Q 30/018* (2013.01)

(58) Field of Classification Search
USPC .......................................... 382/100; 705/317
See application file for complete search history.

(56) References Cited

U.S. PATENT DOCUMENTS

| | | | |
|---|---|---|---|
| 4,917,503 A | 4/1990 | Bhattacharjee | |
| 5,057,434 A | 10/1991 | Prusik et al. | |
| 6,119,932 A | 9/2000 | Maloney et al. | |
| 6,544,925 B1 | 4/2003 | Prusik et al. | |
| 7,209,042 B2 | 4/2007 | Martin et al. | |
| 7,430,588 B2 * | 9/2008 | Hunter | ........................... 709/218 |
| 7,490,575 B2 | 2/2009 | Taylor et al. | |
| 7,562,811 B2 | 7/2009 | Nemet et al. | |
| 7,571,695 B2 | 8/2009 | Taylor et al. | |
| 7,809,152 B2 | 10/2010 | Zhao et al. | |
| 8,091,776 B2 | 1/2012 | Nemet et al. | |

(Continued)

FOREIGN PATENT DOCUMENTS

| | | |
|---|---|---|
| EP | 0 117 390 | 9/1984 |
| WO | 2007114976 | 10/2007 |
| WO | WO2011057695 | 5/2011 |

OTHER PUBLICATIONS

Teskey, M., "Turning RFID Data into Information", 2008, downloaded Feb. 23, 2010.

(Continued)

*Primary Examiner* — Kira Nguyen
(74) *Attorney, Agent, or Firm* — K&L Gates LLP

(57) ABSTRACT

Computing systems and methods for electronically indicating the acceptability of a product. An image capture and communication device may analyze a product label that includes one or more monitors, authentication elements, and identification elements. The image capture and communication device may determine the type and features of the monitors, authentication elements, and identification elements and, based on the type of the monitors, authentication elements, and identification elements. The image capture and communication device may transmit data based on the type and features to a host server, which may transmit data associated with the host product to the image capture and communication device in, inter alia, the form of an acceptability report.

32 Claims, 12 Drawing Sheets

(56) References Cited

U.S. PATENT DOCUMENTS

| | | | |
|---|---|---|---|
| 8,196,821 B2 | 6/2012 | Nemet et al. | |
| 2003/0165602 A1 | 9/2003 | Garwood | |
| 2003/0216969 A1 | 11/2003 | Bauer et al. | |
| 2005/0011957 A1* | 1/2005 | Attia et al. | 235/462.46 |
| 2005/0198095 A1* | 9/2005 | Du et al. | 709/200 |
| 2006/0034602 A1 | 2/2006 | Takaaki | |
| 2006/0157559 A1 | 7/2006 | Levy et al. | |
| 2006/0200480 A1* | 9/2006 | Harris et al. | 707/101 |
| 2007/0012784 A1 | 1/2007 | Mercolino | |
| 2007/0160814 A1* | 7/2007 | Mercolino | 428/195.1 |
| 2007/0235528 A1 | 10/2007 | Spencer et al. | |
| 2007/0274561 A1 | 11/2007 | Rhoads et al. | |
| 2008/0156876 A1 | 7/2008 | Vinogradov | |
| 2008/0253648 A1* | 10/2008 | Mulder et al. | 382/165 |
| 2008/0298472 A1 | 12/2008 | Jain et al. | |
| 2009/0063307 A1 | 3/2009 | Groenovelt et al. | |
| 2009/0207881 A1* | 8/2009 | Nakatani | 374/162 |
| 2009/0327258 A1* | 12/2009 | Lou et al. | 707/4 |
| 2010/0051707 A1* | 3/2010 | Conzelmann | 235/494 |
| 2010/0119158 A1 | 5/2010 | Dalal et al. | |
| 2010/0219235 A1* | 9/2010 | Nemet et al. | 235/375 |
| 2010/0293106 A1 | 11/2010 | Rhoads et al. | |
| 2010/0327051 A1 | 12/2010 | Lyon et al. | |
| 2011/0006109 A1 | 1/2011 | Nemet et al. | |
| 2011/0006115 A1 | 1/2011 | Nemet et al. | |
| 2011/0007151 A1* | 1/2011 | Goldberg | 348/135 |
| 2011/0050872 A1 | 3/2011 | Harbert et al. | |
| 2011/0258130 A1 | 10/2011 | Grabiner et al. | |

OTHER PUBLICATIONS

Apple—iPhone—Technical Specifications, downloaded on Mar. 31, 2010.

"Will Serialization Make Authentication Obsolete?", 5th Global Forum on Pharmaceutical AntiCounterfeiting, Feb. 2010, Miami, Florida, presented by Jim Rittenburg.

"Barcode", downloaded from Wikipedia on Feb. 22, 2010.

Van Arnum, P., "Epedigree in the Pharmaceutical Supply Chain", 2008, downloaded on Feb. 23, 2010.

iPhone User Guide, for iPhone OS 3.1 Software. Apple, Inc. (2009).

"Security Inks", International Paper Knowledge Center, downloaded Mar. 11, 2010.

The International Search Report and Written Opinion issued for International Application No. PCT/US2011/001158, dated Nov. 3, 2011.

McGraw-Hill Book Company, McGraw-Hill Yearbook of Science & Technology, 1987, pp. 205-206.

Zall, et al., "Evaluation of Automated Time Temperature Monitoring System in Measuring Freshness of UHT Milk," Dairy and Food Sanitation, vol. 6, No. 7 (Jul. 1986), pp. 285-290.

Anonymous, "'Smart' labels: tracking products and freshness," Modern Material Handling (1986), pp. 2-5.

Fields and Prusik, "Shelf life estimation of beverage and food products using bar coded time-temperature indicator labels," The Shelf Life of Food and Beverages (1986), p. 23.

Lifelines, Computerizing Shelf Life Analysis, Product Information (1989).

PCT Search Report and Written Opinion dated Jan. 9, 2013 issued for International PCT Application No. PCT/ US12/58699.

Covectra. Multi-Layered Brand Protection. Unit Level Serialization and Mobile/Smartphone Authentication, presentation given by Steve Wood, President of Covectra at the 5th Global Forum on Pharmaceutical Anti-counterfeiting, Feb. 2010.

PharmaSecure. Product Security, Branding, and Marketing for Emerging Markets, presentation material at 5th Global Forum on Pharmaceutical Anti-counterfeiting, Feb. 2010.

Brand Protection and Market Intelligence for Cash-Based Societies, Sproxil, presentation material at 5th Global Forum on Pharmaceutical Anti-counterfeiting, Feb. 2010.

Consortium Reports Successful Drug Tracking and Authenticating Pilot, by daphne, PMPNews.com, Mar. 5, 2010, downloaded on Jul. 30, 2012.

Basta, "Brand Protection Technology Takes a Patient-Communication Turn", PC Pharmaceutical Commerce, Mar. 3, 2010, downloaded on Jul. 30, 2012.

Healthcare & Life Sciences. Pharmaceuticals & Medical Devices, resentation material at 5th Global Forum on Pharmaceutical Anti-counterfeiting, Feb. 2010.

* cited by examiner

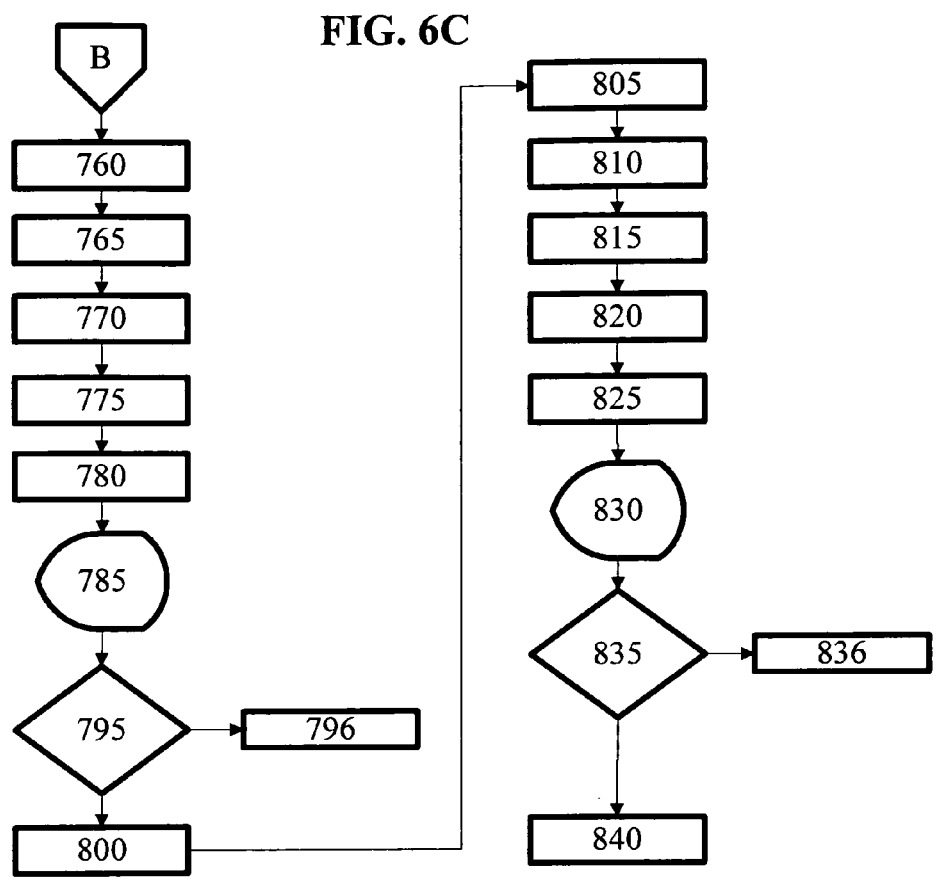

COMPUTING SYSTEMS AND METHODS FOR ELECTRONICALLY INDICATING THE ACCEPTABILITY OF A PRODUCT

FIELD OF THE INVENTION

The present invention relates to computing systems and methods for electronically indicating the acceptability of a product.

BACKGROUND OF THE INVENTION

Medical and health care products are usually marked with a "shelf life expiration" or "use by" date to enable medical practitioners, healthcare workers, patients and the public to determine whether or not to use a medical or healthcare product. The expiration date is generally marked prominently displayed on the product label. The label may also contain a variety of additional information, including product name, manufacturer name, location and date of manufactures, lot/batch number, and storage conditions. Meats, fish and other food products obtainable at a supermarket are usually marked with a "sell by" or "use by" date to help customers to consume or otherwise use the food products while it is still acceptably fresh. In the case of fresh or frozen meats and fish, the "sell by" or "use by" date is generally marked on a label which is prominently displayed on the product. The label can also contain a variety of additional information, including a product description, price information, weight information, and nutritional information. Other perishable products including various personal care products, and industrial products can also bear a "use by" date.

Monitors are devices used to track the exposure of a host product to one or more particular conditions, such as, temperature. Monitors, such as environmental monitors, may be calibrated to indicate the presence of certain environmental conditions, or when certain environmental conditions surpass pre-set limits. Some monitors provide a visual or electronic signal to make such indications.

Use of monitors in product labels can give consumers, patients or other end users some assurance that a given product is acceptable for use by providing some degree of protection against using products that may be ineffective or spoiled because of aging or adverse conditions.

Other factors can also detract from the acceptability of commercial products. For example, a product may be counterfeit and have little or no acceptability. Some measures taken to prevent or identify counterfeit products include various track-and-trace methods which can trace the movement of a product from its manufacturer or other legitimate source to a consumer or other user to assure authenticity. Radio-frequency identification (RFID) and barcodes are two technology methods which can be used to help implement traceability. RFID devices can be incorporated in packages, package labeling, or other product labeling.

Regulatory agencies in the United States and elsewhere have implemented—or are contemplating implementing—"pedigree" requirements for pharmaceutical products. A pedigree is, for example, a certified record that contains information about each distribution of a prescription drug which can be electronically embodied in what is known as an "epedigree".

SUMMARY OF THE INVENTION

In certain embodiments, the present invention may provide a method comprising analyzing by an image capture and communication device a product label for a host product, the product label comprising at least two of one or more environmental monitors, one or more authentication elements, and one or more identification elements, determining by the image capture and communication device a type and one or more features based on the type for each of the at least two of the one or more environmental monitors, one or more authentication elements, and one or more identification elements, accessing by the image capture and communication device a host server, transmitting by the image capture and communication device to the host server data based on the type and features for each of the at least two of the one or more environmental monitors, one or more authentication elements, and one or more identification elements, receiving by the image capture and communication device from the host server an acceptability report based on the data for the at least two of the one or more environmental monitors, one or more authentication elements, and one or more identification elements, and outputting by the image capture and communication device the acceptability report.

In another embodiment, the present invention may provide a method comprising receiving by a host server one or more messages from one or more image capture and communication devices, the one or more messages including one or more acceptability for use data having authenticity, product identity, and current environmental data for one or more host products, determining by the host server whether the host server has access to at least one environmental history for each of the one or more host products, tabulating by the host server one or more second messages including one or more second acceptability for use data for the one or more host products, wherein the one or more second acceptability for use data is tabulated based on the acceptability for use data and, if the host server has access to at least one environmental history for each of the one or more host products, the at least one environmental history foe each of the one or more host products, and transmitting by the host server to the one or more image capture and communication devices the one or more second messages.

BRIEF DESCRIPTION OF THE DRAWINGS

Features and other aspects of embodiments of the present invention are explained in the following description taken in conjunction with the accompanying drawings, wherein:

FIG. 6C illustrates a method according to another aspect of the present invention;

The drawings are exemplary, not limiting. It is intended for items that are labeled with the same number in multiple figures to refer to the same item throughout the figures.

DETAILED DESCRIPTION

Various embodiments of the present invention will now be described in greater detail with reference to the drawings.

Figure 1:
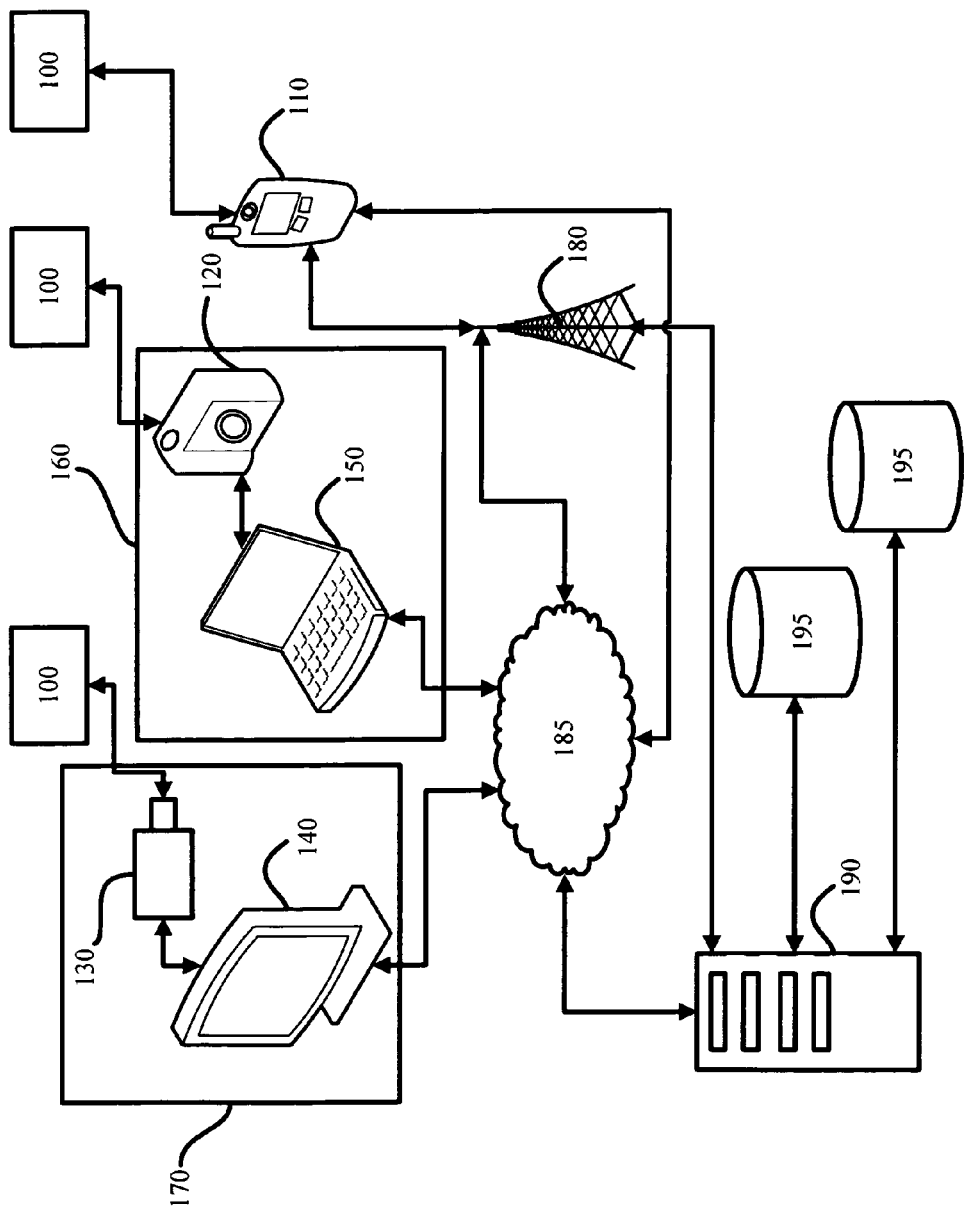
FIG. 1 illustrates a system according to one aspect of the present invention.

As shown in FIG. 1, one aspect of the present invention may include one or more image capture and communication devices 170, 160 and 110 directly and indirectly connected to one or more host servers 190 through network 185 or cellular network 180. Host servers 190 may be directly or indirectly connected to one or more databases 195. Image capture and communication devices 170, 160, and 110 may receive data from one or more product labels 100.

In one aspect, an image capture and communication device may be any single or set of hardware equipment that is encoded and able to analyze product labels 100 and transmit data collected from the analysis through network 185 or cellular network 180 to host servers 190. The image capture and communication device may include one or more non-transitory data storage devices, such as harddrives, RAM, ROM, CD-ROM, DVD-ROM, floppy-disk drives, and/or solid-state memory drives; one or more input devices, such as a keyboard, touchpad, mouse, camera, video camera, image scanner, barcode scanner, densitometer, spectrometer, and/or RFID reader; one or more central processing units (CPUs); one or more output devices, such as a display, disc drive, and/or solid-state memory drive; one or more input/output (I/O) communications ports, such as an infrared port, universal serial bus port, serial port, ethernet port, celluar port, HDMI port, Display port, modem port, Bluetooth port, and/or wireless networking controller. The hardware may be in communication with one another by a shared data bus and/or by dedicated connections. The image capture and communication device may have one or more memory with at least one region for storing computer executable program code and one or more CPUs for executing the program code stored in the memory.

The executable program code may include instructions for reading authentication elements, monitors, and identification elements. The executable program code may include instructions to store data based on the image capture and communication device's review or communication with authentication elements, monitors, and identification elements. The executable program code may include instructions to communicate with a host server, transmit the data to the host server, receive data in response to that transmission, and generate and display a report based on the received data. The executable program code may include instructions to generate a report based on the data obtained from the image capture and communication device's review or communication with the authentication elements, monitors, and identification elements. The executable program code may include instructions to output an interrogation signal to an RFID and to receive and/or interpret the data from the RFID. The executable program code may include instructions to read a one-dimensional, two-dimensional, and/or three-dimensional barcode to receive and/or interpret data from the barcode. The executable program code may include instructions to find and recognize patterns in a particular image. For example, the executable program code may find a section of an image which is similar to a stored template, such as a template of a geometrical pattern, for instance, a circle. After the desired pattern is located, the pattern can be further analyzed, for example, to interpret the light and dark pixels of a bar code. Such instructions may include routines from a pattern recognition software library, for example, Matrox Imaging Library, which contains routines for image analysis and bar code reading.

In one aspect, the executable program code includes instructions to store-and-forward data. Such an aspect may include the image capture and communication device's temporarily storing of data in one or more memories for transmission at a later time, for example, when the host server becomes available, when a network or cellular network becomes available, and/or when transmission price rates decrease.

The executable program code may include instructions for capturing separate values for red, green, and blue (RGB) optical spectral ranges and converting the captured separate values into other color spaces for comparison. For example, grayscale, which is the average of RGB value; or cyan OD, which is the negative of the logarithm to the base 10 of the R value expressed as a fraction of its full-scale value.

In one aspect, the image capture and communication device 110 is a mobile phone with a built-in camera and/or video camera, such as Apple's iPhone® smartphones or Research in Motion Ltd.'s BLACKBERRY® smartphones. For example, Apple's iPhone® 3G or 3Gs or Research in Motion's BLACKBERRY® Bold 9700 or Curve™ 8300. In another aspect, the image capture and communication device 160 includes a computer 150 connected to a camera 120. In another aspect, the image capture and communication device 170 includes a computer 140 connected to a camera 130. Computers 140 and 150 may be a computer that generally includes one or more data storage devices, one or more CPUs, one or more input devices, one or more output devices, one or more I/O communications ports, and other hardware components that facilitate performance of the functions of computers 140 and 150. Computers 140 and 150 may be a tablet PC; alternatively, computers 140 and 150 may be a laptop computer. Cameras 120 and 130 may be any camera that is directly or indirectly connected to computer 150. For example, cameras 120 and 130 may be a digital camera connected via USB port or camera 120 and 130 may be a video camera connected to computers 140 and/or 150 by removing a solid-state memory card from cameras 120 and/or 130 and placing it in a solid state memory card reader that is connected to computers 140 and/or 150. Camera 120 and/or 130 may be built into or mounted on computers 140 and/or 150. In another aspect, an image capture and communication device may include a smart phone tethered to computers 140 and/or 150. Cameras 120 and/or 130 may be connected to a smart phone by removing a solid-state memory card from cameras 120 and/or 130 and placing it in a solid state memory card reader that is connected to the smart phone.

Network 185 may include any type of network infrastructure, such as client/server, peer-to-peer, or hybrid architectures. Network 185 may include the Internet. In one aspect, cellular network 180 is any cellular network. Cellular network 180 may operate under any mobile telephony standard such as 0G, 1G, 2G, 2G transitional, 3G, 3G transitional, and/or 4G. Cellular network 180 may be directly or indirectly connected to network 185 and/or host servers 190.

One or more host servers 190 may be one or more remote computer systems that are accessible over a remote or local network or the Internet, such as network 185, or through wireless network infrastructures, such as cellular network 180. Host servers 190 may have all of the hardware attributes of computers 140 and 150. Host servers 190 may be distributed over two or more physical locations. Host servers 190 may include—or be directly or indirectly connected to—one or more databases 195. One or more databases 195 may be any type of database, such as analytic, operational, hierarchical, network, or relational databases. For example, Microsoft SQL Server, MySQL, Oracle Database, Microsoft Access, Microsoft Excel file, and/or comma separated value or tab-delineated file. In another aspect, databases 195 may be—or include—any type of data structure, or nested data structures, such as tables, stacks, queues, lists, linked-lists, arrays, trees, and/or heaps.

Product label 100 may be any product or package label that has one or more monitors, authentication elements, and/or identification elements. Product label 100 may be associated with one or more host products. For example, product label 100 may be placed on—or part of—the product itself, the product's packaging, or the carton, box, crate, or pallet that houses multiple products for shipping, or be stand-a-lone. For example, in one aspect, the product label may travel with a truck driver and be associated with one or more host products on the truck.

Examples of host products include perishable health care products, for example vaccines, drugs, medicaments, pharmaceuticals, cosmeceuticals, nutricosmetics, nutraceuticals, and functional foods, medical devices and prophylactics; biological materials for industrial or therapeutic uses, for example cultures, organs and other human or animal body parts, blood and perishable blood products; diagnostic devices, kits and ingredients containing perishables; batteries and battery containing devices and appliances; foodstuffs including fresh or prepared fish, meats, dairy products, fruits, vegetables, baked goods, desserts and the like; food service products, including restaurant service foods; gourmet products; perishable animal foods; cut and uncut flowers; cosmetics, for example cosmetics containing biologics or other labile ingredients; beauty aids; perishable munitions and ordnance; perishable decontamination packs and products; and liquors, for example, wine, beer, champagne, port, whisky, cognac.

Figure 2A:
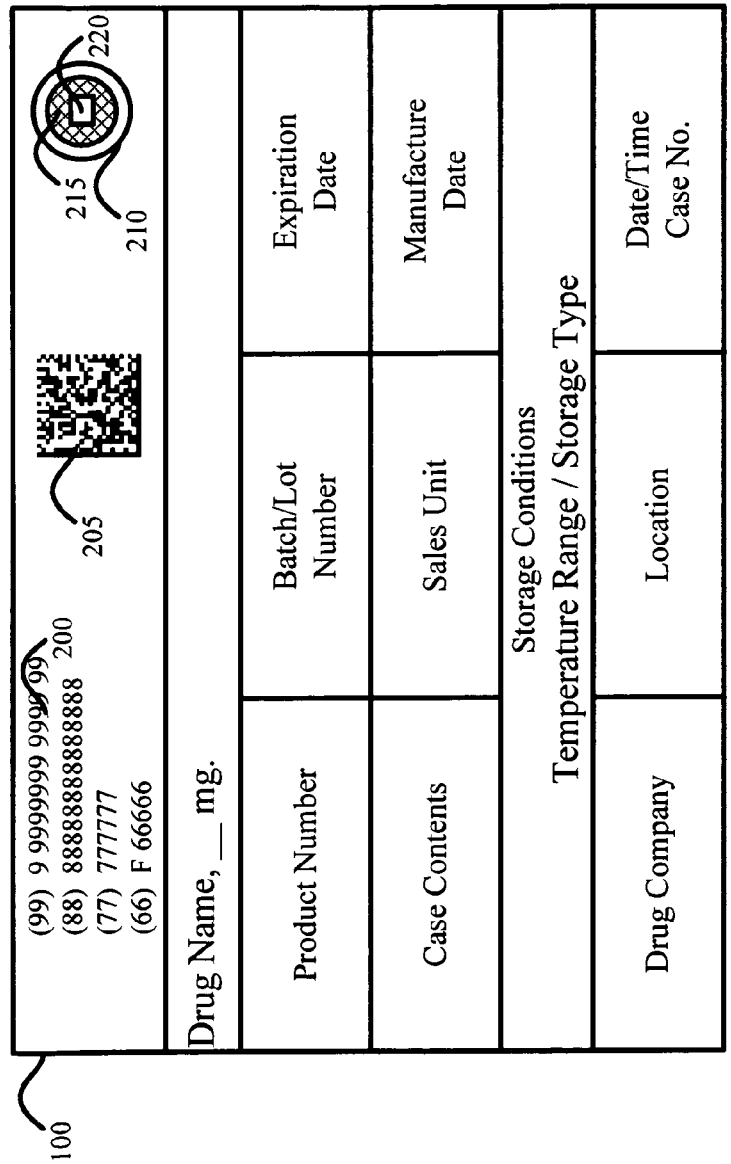
FIG. 2A illustrates a product label 100 according to one aspect of the present invention.
Figure 2B:
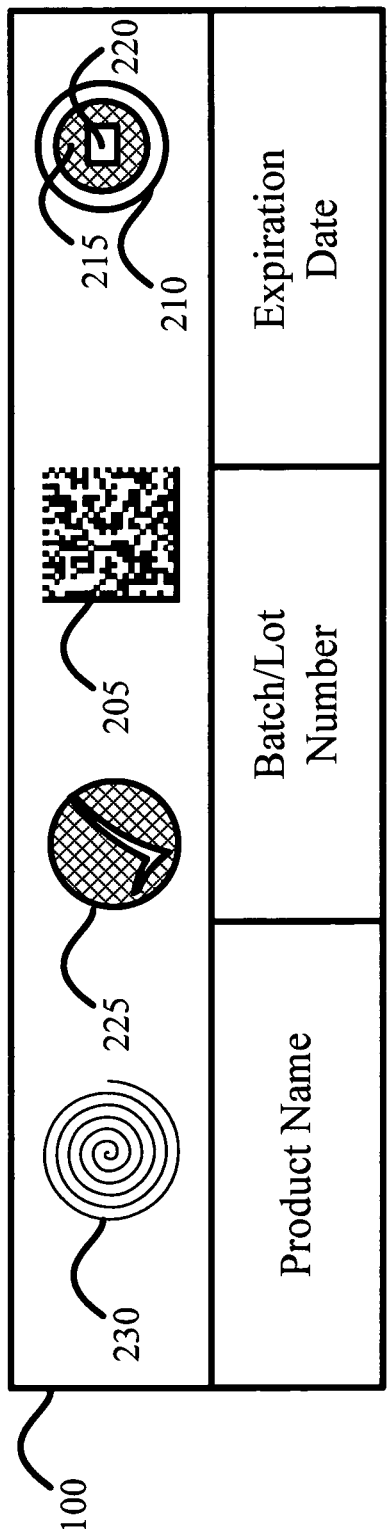
FIG. 2B illustrates a product label 100 according to another aspect of the present invention.

As shown in FIGS. 2A and 2B according to one aspect of the present invention, product label 100 may include one or more of monitors 210 and 225, authentication element 230, and/or identification elements 200 and 205.

The monitors may be environmental history monitors. An environmental history monitor may indicate one or more conditions of the environmental history of the host product which it is associated, for example, the environmental history monitor may indicate past exposure of the host product to one or more environmental conditions. The environmental history monitor's appearance may change with time to indicate the changing value of a monitored condition.

One example of an environmental condition which can be monitored by the environmental history monitor is heat exposure. The environmental history monitor can monitor heat exposure, either as an average cumulative temperature or as the occurrence of a temperature either above or below a specific temperature for a particular duration. Examples of such heat monitoring environmental history monitors may include cumulative time-temperature indicators, freeze indicators, thaw indicators and threshold indicators which can indicate a single event of past exposure to a temperature above ambient.

Other environmental conditions which environmental history monitors may monitor include humidity, mechanical shock, gas exposure, oxygen exposure, toxin exposure, chemical exposure, biological agent exposure, actinic radiation exposure, x-ray exposure, and/or microwave exposure.

Product label 100 may include multiple environmental monitors, each of which monitors a different environmental condition. For example, product label 100 may include two or more of a cumulative time-temperature indicator, a freeze indicator, and a threshold indicator. Product label 100 may include a cumulative time-temperature indicator, a freeze indicator, and a threshold indicator. Other environmental history monitors besides, or in addition to, one or more heat exposure indicators can be included, if desired.

A monitor may include a time-temperature indicator (TTI) composed of colorless diacetylene monomers which develop color as they polymerize. The progressive color development occurs at a rate that increases with temperature.

A monitor may include a multifunctional TTI which integrates two indicator types into a single device. For instance, it may include both a primary indicator, which can develop a color change as a result of cumulative time-temperature exposure, and a secondary indicator, which may be set to trigger at a predetermined temperature.

A monitor may include an activatable TTI system that includes a color-forming time-temperature indicator system that may be affixed to a product label so that the indicator composition is coextensive with a barcode. Upon expiration of the useful shelf life of a host product, the color density may reach a level which obscures the barcode sufficiently to register in market computer systems as a failed or unsafe product.

A monitor may include a combination RFID and environmental condition indicator tag. Information supplied by the RFID, for example, product ID and related data, may be machine read by interrogation of the RFID at an inspection station and the visual condition indication may be optically read by machine at the same station. The signals can be utilized locally at the inspection station or may be used at locations remote therefrom. Alternatively, the environmental condition indicator may have electrical properties that may be read by the RFID device. For example, such an indicator could be one based on the etching of an aluminum film by an acid.

The solid-state polymerization of diacetylene monomers and co-precipitated monomers to polymers are useful as TTIs. The monomers can be prepared as active agents on a substrate, or could be activated on demand by a number of methods including solvent evaporation, melt recrystallization, acid formation, metal formation, salt formation or the associated removal of the acid, metal or salt.

TTIs can include an immobilized enzyme which can react with the substrate to produce a color change in time and temperature dependent manner. Photo induced coloration by radiation of spiropyrans having a temperature dependent decoloration can be used as a TTI.

TTIs can include an upper layer carrying a first reactant and a base layer carrying a second reactant adapted to react with the first reactant upon triggering. TTIs can be formed from thermal paper and an activating film placed on the thermal paper. An indicator can be mixed with a portion of the food product and detects food spoilage directly, for example, pH change, through, for instance, detecting m-nitrophenol, p-nitrophenol and litmus changes from green to red/pink.

A TTI may have two surfaces that remain adhered when brought together: an acid-base indicator in one and an activator in the other. A TTI can be based on an azo coupling reaction between a capped diazonium component and a coupling component. An enzyme based TTI including urease to consume urea to generate ammonia and carbon dioxide, which may cause a pH change causing color change in a pH indicator.

TTIs can be prepared from a free radical-sensitive dye and peroxide on a carrier. TTIs can include a diffusion layer capable of transition above a defined temperature. An indicator film can be placed on one side of diffusion layer and be separated from a reactant material capable of producing a color change when in contact with the indicator film.

TTIs can be produced using vapor permeation techniques. Activatable TTI can include an oxygen-sensitive dye coating and a removable oxygen barrier over the coating.

TTIs having a colorless leuco base and a photoacid can be activated by UV light. TTI devices can include a substrate with organic silver salt oxidizing agent, reducing agent, and indicating indicia. TTIs can also contain a viscoelastic material, barrier material, and porous matrix.

In one aspect, the authentication element may establish or verify the authenticity of the host product with which the monitor is associated. The authentication element may be readable by a human. For example, the authentication element can include an area printed with a special ink, a symbol, or an object which is difficult to reproduce and which, in other aspects, may also visually change with time. The authentication element may be incorporated into the identification element and/or monitor. The identification element may include information referencing the authentication element. If such information, for example, fails to verify the authentication element, label 100 may indicate that the host product is not authentic.

In one aspect, the identification element indicates the identity of the host product. For example, an identification element may include a one-dimensional barcode, a two-dimensional barcode, a three dimensional barcode, or an RFID device. The identification element can be printed and be visible to a human and/or machine-readable. For example, the identification element can be printed with an ink that reflects primarily in the near-infrared and can be read with a charge-coupled device (CCD) camera that is sensitive to near infrared light. The identification element can be accompanied by a human readable equivalent of the identification element, for example a string of text, icons, pictographs or other human-recognizable graphics or symbols.

The identification element may be unique and identifies the host product with which it is associated. The identification element may include an item identifier that indicates the identity of a specific individual host product for example a stock-keeping unit.

In one aspect, the identification element may include a serial global trade identifier number (SGTIN). For example, a "SGTIN-96" tag. A SGTIN-96 tag data specification provides six fields that are to be set for each tag and the combination of all six fields ensures each tag's uniqueness. The six fields are as follows: a header comprising 8 bits; a filter, comprising three bits which can specify if the tagged object is an item, case or pallet; a partition, which is three bits and indicates how the subsequent fields are divided to get the correct data for each; a company prefix, which comprises 20-40 bits (depending on the partition); an item reference, comprising 24-4 bits (depending on the partition) which can comprise the item's global trade identification number "GTIN"; and a serial number, which is 38 bits and contains the item's unique serial number.

The identification element may be compatible with an e-pedigree code used for pharmaceutical tracking. In one aspect where the identification element includes an RFID or other electronic device, the identification element may include an electrical or optical device to read the other elements of product label 100, such as one or more monitors 210 and 225 and/or authentication element 230. Monitors, such as environmental history monitors, may generate both electrical and visual signals indicating exposure to one or more environmental conditions. Such electrical signals may be output to an associated RFID that otherwise acts as a identification element.

The information from monitors 210 and 225, authentication element 230, and identification elements 200 and 205 of product label 100 may be accessible by photocapture, scanning, pattern recognition, image comparison, such as by using image capture and communication devices 110, 160 and 170, or by human recognition.

As shown in FIG. 2A according to one aspect of the present invention, product label 100 may be configured for attachment to a case containing one or more sales units of a pharmaceutical product. Product label 100 may be self-adhesive or otherwise attachable to the case. Product label 100 may be printable in a single pass or in multiple passes. The entire label 100 may be printable. One or more monitors, authentication elements, and/or identification elements may be separately fabricated and then attached or applied to label 100. It is noted that product label 100 may include one or more monitors, authentication elements, and/or identification element that are not physically embedded or otherwise located on the same surface or housing; however, in such an aspect, the monitors, authentication elements, and/or identification elements would be associated with the same one or more host products.

As shown in FIG. 2A according to one aspect of the present invention, label 100 may include in a header row at the top of the label, identification element 200, a two-dimensional barcode 205, and monitor 210. Beneath the header row, the label has the drug name and strength, prominently displayed. Beneath the drug name appear additional data, such as, a product or list number, for example, 1 55Z5555 555 555; a batch or a lot number, for example, F 66666; an expiry date for the drug or other host product; a notation as to the case contents, for example, 10 units per case; a sales unit description, for example, 2 syringes per carton; a date of manufacture of the drug; storage conditions such as a permissible range of temperature variation and a storage type, for example, refrigerated storage; the name of the supplier; the location of the manufacturing plant; and the date and time of dispatch and a case number, for example, 72/1000. Identification element 200 may include a product number which may be the same as or different from the product/list number. The identification element 200 may be the same as or different from the product expiration date and a batch or lot number. Some or all of the information in identification element 200 may be encoded into identification element 205.

Identification element 205 can include one or more authentication elements, for example, a serial number or a code correlated with other information on label 100, which uniquely identifies the host product unit, for example, a case, and hinders counterfeiting. Authentication element 230 may include one or more identification elements. In another aspect, monitors 210 and/or 225 may include one or more identification and/or authentication elements.

In one aspect, monitor 210 is an environmental history monitor that operates as a TTI. Monitor 210 may include two color zones: an active zone 220 and a reference zone 215. Active zone 220 can change color. For example, active zone 220's color may darken in response to cumulative temperature exposure over time outside of acceptable limits for the host product. If active zone 220 appears as dark or darker than reference zone 215, monitor 220 is indicating by visual signal that the host product with which it is associated is no longer acceptable for use. In other aspects, active zone 220's color may lighten in response to cumulative temperature exposure over time outside of acceptable limits for the host product. In such an aspect, if active zone 220 appears lighter than reference zone 215, monitor 220 is indicating by visual signal that the host product with which it is associated is no longer acceptable for use. In another aspect, any suitable color value, or combination of color values, detectable in active zone 220 and reference zone 215 may be compared, for example, grayscale reflectivity, grayscale density, color optical density, RGB values, Lab values, brightness, hue and/or color intensity.

Figure 3:
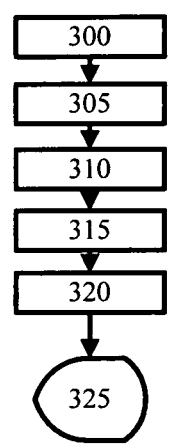
FIG. 3 illustrates a method according to one aspect of the present invention.

As shown in FIG. 3 at step 300, in one aspect of the present invention, an image capture and communication device may analyze a product label 100 (as shown in FIGS. 1, 2A, and 2B) for a host product. Based on its analysis, for example, by scanning for visual or electronic signals indicative of one or more authentication elements, monitors, and/or identification elements present on product label 100, the image capture and communication device determines a type and one or more features for each of the one or more authentication elements, monitors, and/or identification elements, as shown at step 305.

In one aspect, the type of an authentication element, monitor, or identification elements indicates to the image capture and communication device how the image capture and communication device may retrieve data from the authentication element, monitor, or identification element. For example, the type of an identification element may be a one-dimensional barcode, which may indicate to the image capture and communication device to scan the barcode and interpret the barcode data. In another example, the type of a monitor may be an environmental monitor with an active zone and a reference zone, which may indicate to the image capture and communication device to capture an image of the two zones for comparison. In another example, the type of an authentication element may be RFID, which may indicate to the image capture and communication device to send an interrogation signal and retrieve the data from the RFID.

The one or more features for each of the one or more authentication elements, monitors, and/or identification elements are features associated with the type of authentication element, monitor, and identification element that are used to provide data stored in the authentication element, monitor, and identification element. For example, if the type of identification element is a one-dimensional barcode, the features may be the lines and/or numbers associated with the barcode. In another example, if the type of monitor is an environmental monitor that includes an active zone and a reference zone, the features of the monitor may be the color of the active zone and the color of the reference zone. In another example, if the type of authentication element is RFID, the features of the authentication element may be the data stored in the RFID.

As further shown in FIG. 3 at step 310 according to one aspect of the present invention, the image capture and communication device may access the one or more host servers 190 (as shown in FIG. 1). The image capture and communication device may accomplish such access by connecting to host servers 190 through network 185 (as shown in FIG. 1) and/or cellular network 180 (as shown in FIG. 1). In other aspects, the image capture and communication device may connect to host servers 190 through a direct satellite link. Once the image capture and communication device is either directly or indirectly connected to the host server, the image capture and communication device may transmit the type and features for each of one or more authentication elements, monitors, and/or identification elements present on product label 100, as shown at step 315. The image capture and communication device may transmit the type and features to the host servers 190 (as shown in FIG. 1) via short message service (SMS) text message, TCP/IP messaging, email, FTP, PIN email, and/or instant message. The image capture and communication device may receive an acceptability report from host servers 190 (as shown in FIG. 1) based on the type and features for each of one or more authentication elements, monitors, and/or identification elements present on product label 100, as shown at step 320. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

As further shown in FIG. 3 at step 325 according to one aspect of the present invention, the image capture and communication device may display the acceptability report. For example, image capture and communication devices 170, 160, and/or 110 may output a text-based and/or graphical-based acceptability report on display devices such as a liquid crystal display (LCD), light emitting diode (LED) display, or cathode ray tube (CRT) display.

The acceptability report may include text, symbols, and/or graphics indicating any of the following: whether the host product is acceptable to use, whether the host product is authentic; product identification data; product history data, including the environmental history of the host product; instructions on how the user should proceed based on the host product's acceptability; pedigree detail, such as, a SGTIN and/or pedigree verification; and whether a new expiration or use-by date is provided based on the environmental exposure. If the host product is a pharmaceutical product, a link to download a patient information sheet may be included. In addition, late breaking warnings as to possible adverse reactions, product recall information, directions, or requests, or a link to such information, may also be included in the report. The acceptability report may include a link for the holder of the host product to re-order or return the host product. Such information may be triggered by data received from the one or more authentication elements, monitors, and/or identification elements.

The acceptability report may be output audibly by the image capture and communication device. For example, the image capture and communication device may use text-to-speech routines or speech libraries located on either the host servers or image capture and communication device. Such aspects may help vision-impaired users understand whether a host product is acceptable to use.

Figure 4:
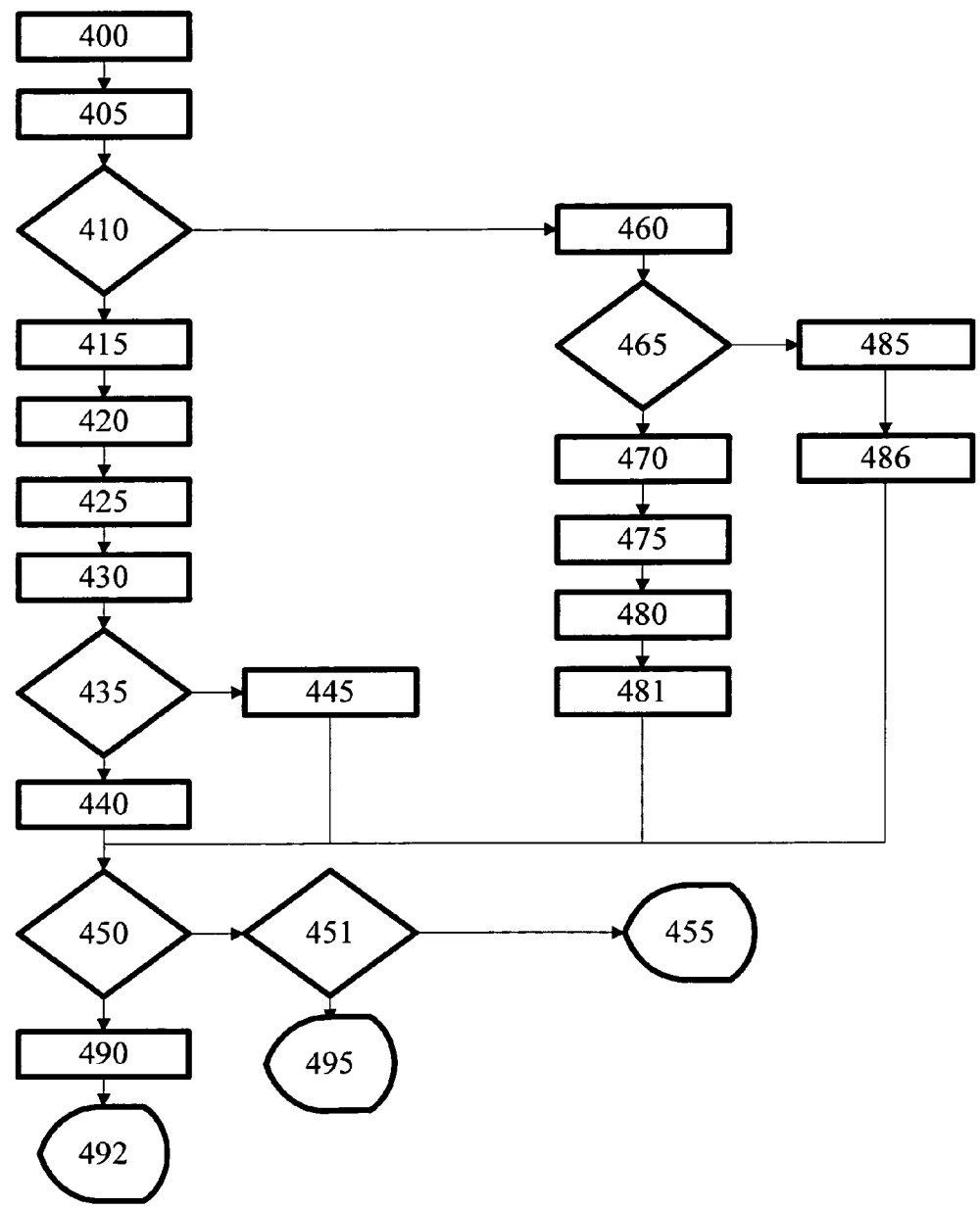
FIG. 4 illustrates a method according to another aspect of the present invention.

As shown in FIG. 4 at step 400, according to one aspect of the present invention, one or more image capture and communication devices 170, 160, and 110 (as shown in FIG. 1) may analyze a monitor with a type and one or more features based on the type for a host product. The one or more image capture and communication devices may take a still picture or image of the monitor. At step 405, the one or more image capture and communications devices may determine the type of monitor and the one or more features based on the type. At step 410, the one or more image capture and communication devices may determine whether the one or more features and/or type indicate that the monitor contains a color reference zone, which has a reference area and an active area, such as are included in monitor 210 (as shown in FIG. 2A).

If the features and/or type indicate that the monitor contains a color reference zone, at step 415, the one or more image capture and communication devices may measure one or more first pixel locations of the reference area and one or more second pixel locations of the active area. In one aspect, the measuring at step 415 is done through executing pattern recognition routines. At step 420, the one or more image capture and communication devices may derive a first RGB value of the reference area based on the one or more first pixel locations and a second RGB value of the active area based on the one or more second pixel locations. At step 425, the one or more image capture and communication devices may convert the first RGB value to a first color space value and the second RGB value to a second color space value. At step 430, the one or more image capture and communication devices may compare the first color space value to the second color space value. For example, color space values may be grayscale, which is obtained by calculating the average of the RGB values. Another color space value example may be cyan OD, which is obtained by calculating the negative of the logarithm to the base 10 of the R value expressed as a fraction of its full-scale value.

At step 435, the one or more image capture and communication devices may determine whether, for example, the still image or picture contains sufficient color resolution for the one or more image capture and communication devices or the one or more host servers 190 (as shown in FIG. 1) to derive color space values accurate enough to provide all available product information from the monitor. For instance, it is possible that if the lighting conditions are poor and the an image capture or communication device may not have created enough light, the image capture and communication device may still have retrieved sufficient data to determine whether the active zone is darker or lighter than the reference zone, but not sufficient data to accurately determine the degree of darkness and lightness necessary to derive more data from the comparison. If the one or more image capture and communication devices determine that the still image or picture does not contain sufficient color resolution, at step 440, the one or more image capture and communication devices may determine whether, based on that comparison (at step 430), the host product is acceptable for use. In further aspects, because of the lack of sufficient color, any acceptability data generated downstream may indicate whether the host product is acceptable, but may not accurately indicate the degree of acceptability, for example, the degree of exposure to a particular condition. In such an aspect, the degrees of acceptability may be omitted from acceptability reports.

If the one or more image capture and communication devices determine that the still image or picture does contain sufficient color resolution, at step 445, the one or more image capture and communication devices may determine whether, based on that comparison (at step 430), the host product is acceptable for use and may indicate the degree of acceptability of use in any acceptability report generated downstream. In one aspect if the active zone's color may darken in response to cumulative temperature exposure over time outside of acceptable limits for the host product. If the active zone's color is as dark or darker than reference zone, the monitor may be indicating by visual signal that the host product with which it is associated is no longer acceptable for use. In another aspect, the active zone's color may lighten in response to cumulative temperature exposure over time outside of acceptable limits for the host product. In such aspects, if the active zone's color is lighter than reference zone's color, the monitor may be indicating by visual signal that the host product with which it is associated is no longer acceptable for use.

If, at step 410, the one or more image capture and communication devices determines that the features and/or type indicate that the monitor does not contain a color reference zone, at step 460, the one or more image capture and communication devices may measure one or more first pixel locations of the active area. In one aspect, the measuring at step 460 is done through executing pattern recognition routines. At step 465, the one or more image capture and communication devices determines, based on the type and/or features of the monitor, whether the monitor provides information, such as environmental condition, by color. If the monitor provides information by color, at step 470, the one or more image capture and communication devices may derive a first RGB value of the active area based on the one or more first pixel locations. At step 475, the one or more image capture and communication devices may convert the first RGB value to a first color space value. At step 480, the one or more image capture and communication devices may compare the first color space value to a set of values based on the type and/or features of the monitor in order to determine if the color space value is less than, equal to, or greater than the set of values. Based on the comparison (at step 480), the one or more image capture and communication devices, at step 481, may determine whether the host product is acceptable for use.

If the monitor does not provide information by color, at step 485, the one or more image capture and communication devices determines whether information is provided by determining a particular visual pattern on the monitor. For example, in one aspect, if certain environmental conditions are present, a symbol may appear in the active area, such as a check mark as shown in monitor 225 in FIG. 2A. At step 486, if the visual pattern is present on the monitor, the one or more image capture and communication devices may determine, based on the visual pattern, whether the host product is acceptable for use. Depending on the type and features of the monitor, the existence of a visual pattern may indicate that a host product is or is not acceptable for use; or, the visual pattern may need to be interpreted in light of other data, such as other data from other monitors, authentication elements, and/or identity elements, in order for the image capture and communication device and/or host servers to determine whether the host product is acceptable for use.

At step 450, the one or more image capture and communication devices determines whether the image capture and communication device is directly or indirectly connected to one or more host servers 190 (as shown in FIG. 1) through network 185 (as shown in FIG. 1). If the one or more image capture and communication devices determines that it is connected to one or more host servers through network 185, the image capture and communication device may, at step 490, transmit data including the type, features, comparison results (at steps 430 and/or 480), and/or determination results (at steps 435, 440, 481, and/or 486) to the one or more host servers. At step 492, the image capture and communication device may receive data from the host server that is associated with the one or more host product that is associated with the monitor and output the data in the form of an acceptability report (as described in step 325 in FIG. 3). Such data may include the host product's name, strength, presentation (for example, pre-filled syringe, vial, ampoule, etc.), quantity, product identification number, serialized numeric identifier (SNI), SGTIN, numeric drug code (NDC), lot number, expiration date, location of manufacture, date of manufacture, storage conditions, date/time and condition of unit from each reading including identification, authentication and monitor, site of reading or GPS information, identity of reading device or person or entity making the reading, product specific information (for example, specifications, package insert, use instructions, etc.), recall status, warranty information, product coupons for discounts, notice of product status change (for example, if the product is subject to a recall or other action, notice could be automatically sent to the last entity reading the acceptability device), notice to reorder product, information and emergency call or e-mail addresses.

If the one or more image capture and communication devices determine that it is not connected to one or more host servers through network 185, at step 451, the one or more image capture and communication devices determine whether they can transmit a message, such as SMS, through cellular network 180 to the one or more host servers. If the one or more image capture and communication devices determine that they can transmit a message, at step 495, the one or more image capture and communication devices may receive data from the host server that is associated with the one or more host products that are associated with the monitor. In one aspect, the data may be in the form of a link, such as a URL, that references a webpage that hosts an acceptability report that the one or more host servers have generated (as described in step 325 in FIG. 3).

If the one or more image capture and communication devices determine that they cannot transmit a message, at step 455, the one or more image capture and communication devices may output to the user an acceptability report based on the results of the comparisons and determinations at steps 430, 435, 440, 480, 481, and/or 486. The output may be in the form of a visual display and/or audible display.

Figure 5:
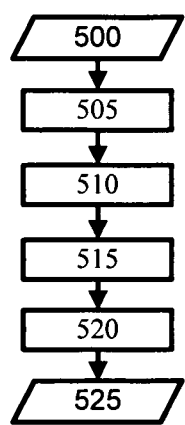
FIG. 5 illustrates a method according to another aspect of the present invention.

As shown in FIG. 5 at step 500, in one aspect of the present invention, one or more host servers 190 (as shown in FIG. 1) may receive a message or other data from one or more image capture and communication devices 170, 160, and 110 (as shown in FIG. 1) including the type and features of each of the one or more authentication elements, monitors, and/or identification elements present on the product label that the image capture and communication device 170, 160, and 110 analyzes. In further aspects, message or data is received via SMS text message, TCP/IP messaging, email, FTP, PIN email, and/or instant message.

As further shown in FIG. 5 at step 505, based on the message or data, the host servers 190 (as shown in FIG. 1) retrieve information about the host product from one or more databases 195 (as shown in FIG. 1) and store the message or data that was received from the image capture and communication device 170, 160, and 110 (as shown in FIG. 1) in databases 195. Information about the host product may include the host product's name, strength, presentation (for example, pre-filled syringe, vial, ampoule, etc.), quantity, product identification number, SNI, SGTIN, NDC, lot number, expiration date, location of manufacture, date of manufacture, storage conditions, date/time and condition of unit from each reading including identification, authentication and monitor, site of reading or GPS information, identity of reading device or person or entity making the reading, product specific information (for example, specifications, package insert, use instructions, etc.), recall status, warranty information, product coupons for discounts, notice of product status change (for example, if the product is subject to a recall or other action, notice could be automatically sent to the last entity reading the acceptability device), notice to reorder product, information and emergency call or e-mail addresses.

In further aspects, at step 510, based on the message or data, the host server 190 (as shown in FIG. 1) may determine, for example, whether the host product is authentic and/or whether the host product was exposed to environmental conditions outside or inside set limits for the host product. At step 515 one or more host servers 190 (as shown in FIG. 1) may store information referencing the determination (made at step 510) in the one or more databases 195 (as shown in FIG. 1) 515. At step 520, host servers 190 (as shown in FIG. 1) may generate an acceptability report based on the determination (made at step 510). In one aspect, generating an acceptability report (generated at step 520) may include generating an HTML-based webpage and a URL pointing to the webpage. At step 525, the host servers 190 (as shown in FIG. 1) may transmit a message or data including the URL to the image capture and communication device via cellular network 180 (as shown in FIG. 1) or network 185 (as shown in FIG. 1).

In another aspect, generating an acceptability report (generated at step 520) may include tabulating data based on the determination (made at step 510) and/or other attributes of the host product. In such an aspect, at step 525, one or more host servers 190 (as shown in FIG. 1) may transmit the acceptability report in the form of such tabulated data to the image capture and communication device 170, 160, and/or 110 (as shown in FIG. 1) via SMS text message, TCP/IP messaging, email, FTP, PIN email, and/or instant message.

Figure 6A:
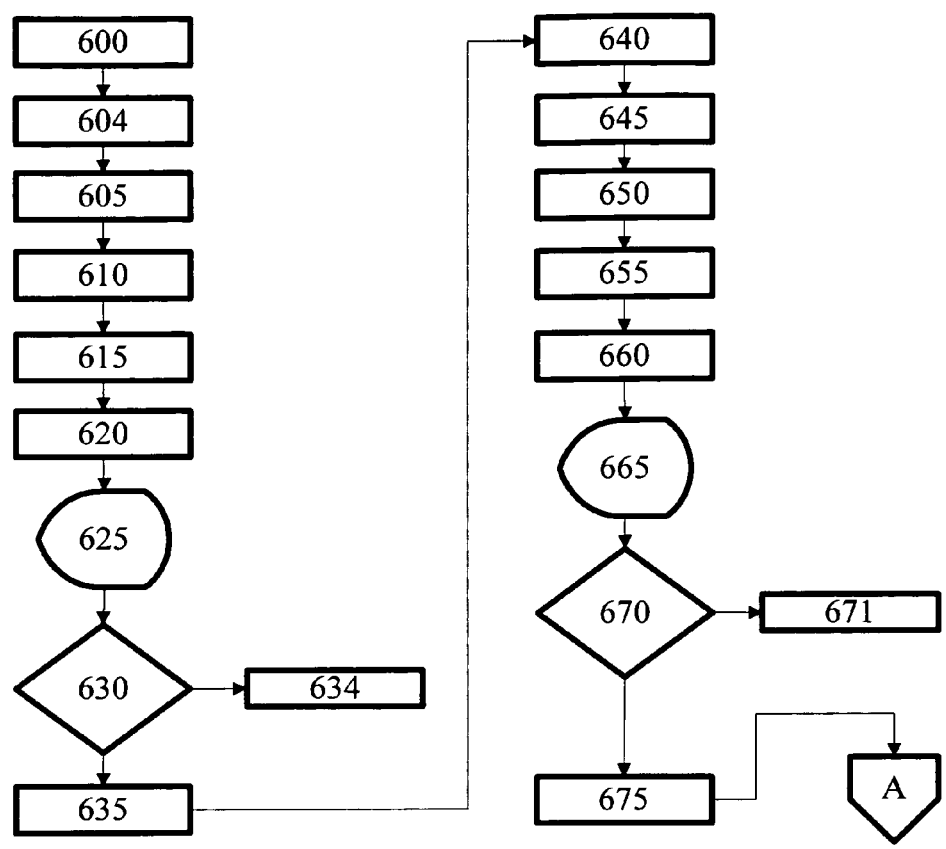
FIG. 6A illustrates a method according to another aspect of the present invention.
Figure 6B:
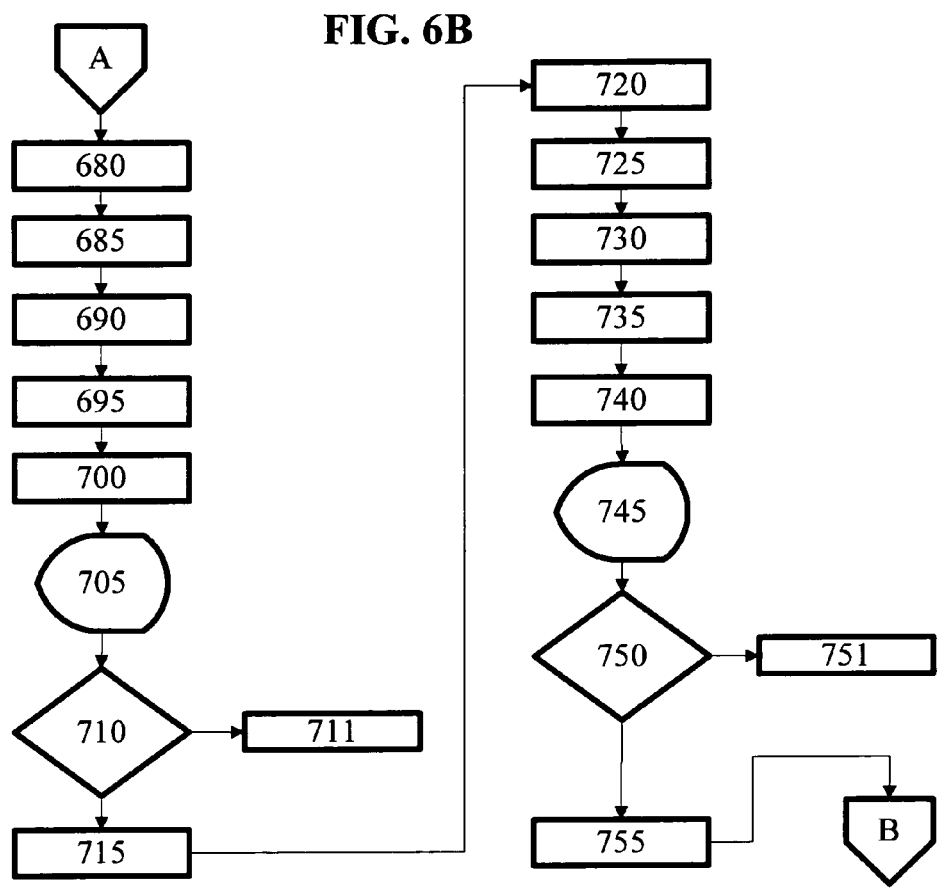
FIG. 6B illustrates a method according to another aspect of the present invention.

As shown in FIGS. 6A, 6B, and 6C, according to one aspect of the present invention a manufacturer of a host product may use systems and methods of the present invention to track the acceptability of the host product throughout the steps of clinical trials of the host product. For example, at step 600, the manufacturer may associate one or more host products with a product label 100 (as shown in FIGS. 1, 2A, and 2B) including at least two of one or more monitors, product identification elements, and authentication elements. During the association (at step 600), the manufacturer may set the limits or other data for each of the one or more monitors, product identification elements, and/or authentication elements; or, the manufacturer may use one or more monitors, product identification elements, and/or authentication elements with pre-set limits and/or data as appropriate for the particular host product.

At step 604, before the manufacturer is ready to release the product for use at a clinical trial, an image capture and communication device may analyze a product label 100 (as shown in FIGS. 1, 2A, and 2B) for a host product at the host product's site of manufacture. Based on its analysis, for example, by scanning for visual or electronic signals indicative of one or more authentication elements, monitors, and/or identification elements present on product label 100, the image capture and communication device determines a type and one or more features for each of the one or more authentication elements, monitors, and/or identification elements, as shown at step 605.

At step 610, the image capture and communication device may access the one or more host servers 190 (as shown in FIG. 1). The image capture and communication device may accomplish such access by connecting to host servers 190 through network 185 (as shown in FIG. 1) and/or cellular network 180 (as shown in FIG. 1). In other aspects, the image capture and communication device may connect to host servers 190 through a direct satellite link. Once the image capture and communication device is either directly or indirectly connected to the host server, the image capture and communication device may transmit the type and features for each of one or more authentication elements, monitors, and/or identification elements present on product label 100, as shown at step 615. The image capture and communication device may transmit the type and features to the host servers 190 (as shown in FIG. 1) via short message service (SMS) text message, TCP/IP messaging, email, FTP, PIN email, and/or instant message. The image capture and communication device may receive an acceptability report from host servers 190 (as shown in FIG. 1) based on the type and features for each of one or more authentication elements, monitors, and/or identification elements present on product label 100, as shown at step 620. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 625 according to one aspect of the present invention, the image capture and communication device may output the acceptability report. For example, image capture and communication devices 170, 160, and/or 110 may output a text-based and/or graphical-based acceptability report on display devices such as a LCD display, LED display, or CRT display. In addition, an audible report may be output in lieu of—or in addition to—the graphically displayed report. At step 630, based on the outputted acceptability report, either the user of the image capture and communication device—or the device itself—may determine whether the host product is acceptable for use. For example, the acceptability report may actually state "it is not acceptable for use" or "it is acceptable use" or provide certain data for interpretation by its user or the device/host servers itself/themselves. At step 634, if the host product is not acceptable for use, it may not be shipped out. In a further aspect, the acceptability report may include instructions transmitted or generated by the manufacturer about what the user should do with an unacceptable product. If the product is acceptable for use, at step 635, the host product is released to a clinic, such as a hospital.

At step 640, the clinic and/or delivery driver may analyze the inbound product label 100 (as shown in FIGS. 1, 2A, and 2B) of the host product at the clinic. Based on its analysis, the image capture and communication device determines a type and one or more features for each of the one or more authentication elements, monitors, and/or identification elements, as shown at step 645.

At step 650, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 655. The image capture and communication device may receive an acceptability report from host servers 190 (as shown in FIG. 1) based on the type and features for each of one or more authentication elements, monitors, and/or identification elements present on product label 100, as shown at step 660. In addition, the acceptability report may also take into account historical information about the host product, including the data collected at the site of manufacture. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 665, the image capture and communication device may output the acceptability report. At step 670, based on the outputted acceptability report, either the user of the image capture and communication device—or the device itself—may determine whether the host product is acceptable for use. At step 671, if the host product is not acceptable for use, it may not be shipped out and returned to the manufacturer. In a further aspect, the acceptability report may include instructions transmitted or generated by the manufacturer about what the clinic should do with an unacceptable product. If the product is acceptable for use, at step 675, the host product may be stored until such time as the clinic decides to release the host product to a patient or practitioner.

At step 680, the clinic may analyze the product label 100 (as shown in FIGS. 1, 2A, and 2B) of the stored host product at the clinic. Based on its analysis, the image capture and communication device determines a type and one or more features for each of the one or more authentication elements, monitors, and/or identification elements, as shown at step 685.

At step 690, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 695. The image capture and communication device may receive an acceptability report from host servers 190 (as shown in FIG. 1) based on the type and features for each of one or more authentication elements, monitors, and/or identification elements present on product label 100, as shown at step 700. In addition, the acceptability report may also take into account historical information about the host product, including the data collected at the site of manufacture and inbound at the clinic. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 705, the image capture and communication device may output the acceptability report. At step 710, based on the outputted acceptability report, either the user of the image capture and communication device—or the device itself—may determine whether the host product is acceptable for use. At step 711, if the host product is not acceptable for use, it may not be distributed to a patient or practitioner for use in the trial and is returned to the manufacturer. In a further aspect, the acceptability report may include instructions transmitted or generated by the manufacturer about what the clinic should do with an unacceptable product. If the product is acceptable for use, at step 715, the host product may be distributed to a patient or practitioner.

At step 720, the patient or practitioner may analyze the product label 100 (as shown in FIGS. 1, 2A, and 2B) of the host product at the practitioner's office, patient's home, or other place where the host product is administered to the patient. Based on its analysis, the image capture and communication device determines a type and one or more features for each of the one or more authentication elements, monitors, and/or identification elements, as shown at step 725.

At step 730, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 735. The image capture and communication device may receive an acceptability report from host servers 190 (as shown in FIG. 1) based on the type and features for each of one or more authentication elements, monitors, and/or identification elements present on product label 100, as shown at step 740. In addition, the acceptability report may also take into account historical information about the host product, including the data collected at the site of manufacture and inbound and outbound at the clinic. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 745, the image capture and communication device may output the acceptability report. At step 750, based on the outputted acceptability report, either the user of the image capture and communication device—or the device itself— may determine whether the host product is acceptable for use. At step 751, if the host product is not acceptable for use, it may not be used or caused to be used by a patient or practitioner in the trial and is returned to the manufacturer. In a further aspect, the acceptability report may include instructions transmitted or generated by the manufacturer about what the clinic should do with an unacceptable product. If the product is acceptable for use, at step 755, the host product may be used—or caused to be used—by a patient or practitioner.

At step 760, the patient or practitioner may withdraw from the clinical trial and return the host product to the clinic. On the host product's return, the clinic may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 765.

At step 770, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 775. The image capture and communication device may receive an acceptability report from host servers 190 (as shown in FIG. 1) based on the type and features for each of one or more authentication elements, monitors, and/or identification elements present on product label 100, as shown at step 780. In addition, the acceptability report may also take into account historical information about the host product, including the data collected at the site of manufacture, inbound and outbound at the clinic, and at the practitioner's office, patient's home, and/or other place the host product was administered to the patient. In a further aspect, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 785, the image capture and communication device may output the acceptability report. At step 795, based on the outputted acceptability report, either the user of the image capture and communication device—or the device itself— may determine whether the host product is acceptable for use. At step 796, if the host product is not acceptable for use, it may not be re-used and thus cannot be redistributed by the clinic or manufacturer and may be returned to the manufacturer for destruction. In a further aspect, the acceptability report may include instructions transmitted or generated by the manufacturer about what the clinic should do with an unacceptable product. If the product is acceptable for use, at step 800, the host product may be returned to the manufacturer for restocking and/or repackaging. In a further aspect, the acceptability report may include instructions transmitted or generated by the manufacturer about what the clinic should do with an acceptable product.

At step 805, on the host product's return, the manufacturer may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 810.

At step 815, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 820. The image capture and communication device may receive an acceptability report from host servers 190 (as shown in FIG. 1) based on the type and features for each of one or more authentication elements, monitors, and/or identification elements present on product label 100, as shown at step 825. In addition, the acceptability report may also take into account historical information about the host product, including the data collected at the site of manufacture, inbound and outbound at the clinic, and at the practitioner's office, patient's home, and/or other place the host product was administered to the patient. In a further aspect, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 830, the image capture and communication device may output the acceptability report. At step 835, based on the outputted acceptability report, either the user of the image capture and communication device—or the device itself—may determine whether the host product is acceptable for use. At step 836, if the host product is not acceptable for use, it may not be re-stocked or repackaged and may be sent for destruction. In a further aspect, the acceptability report may include instructions transmitted or generated by the manufacturer about what the manufacturer should do with an unacceptable product. If the product is acceptable for use, at step 840, the host product may be restocked, repackaged, and/or re-issued to a clinic and/or patient or practitioner In steps 600-840, the one or more image capture and communication devices may be the same image capture and communication devices, different image capture and communication devices, or the same device for some steps and different devices for other steps.

Figure 7A:
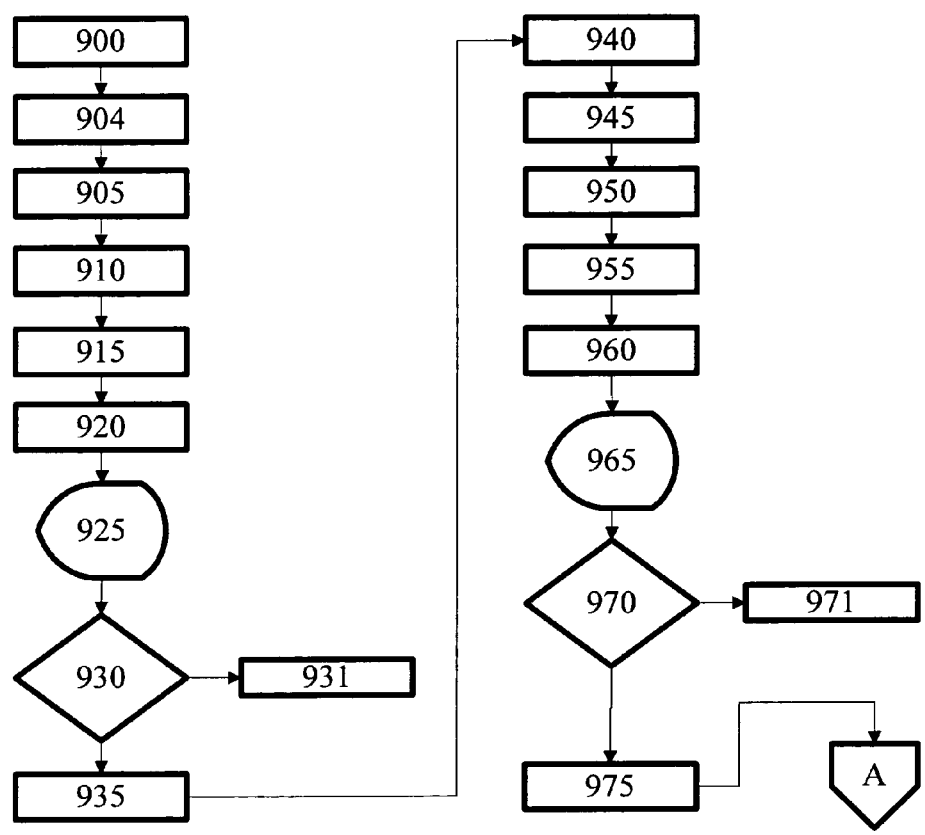
FIG. 7A illustrates a method according to another aspect of the present invention.
Figure 7B:
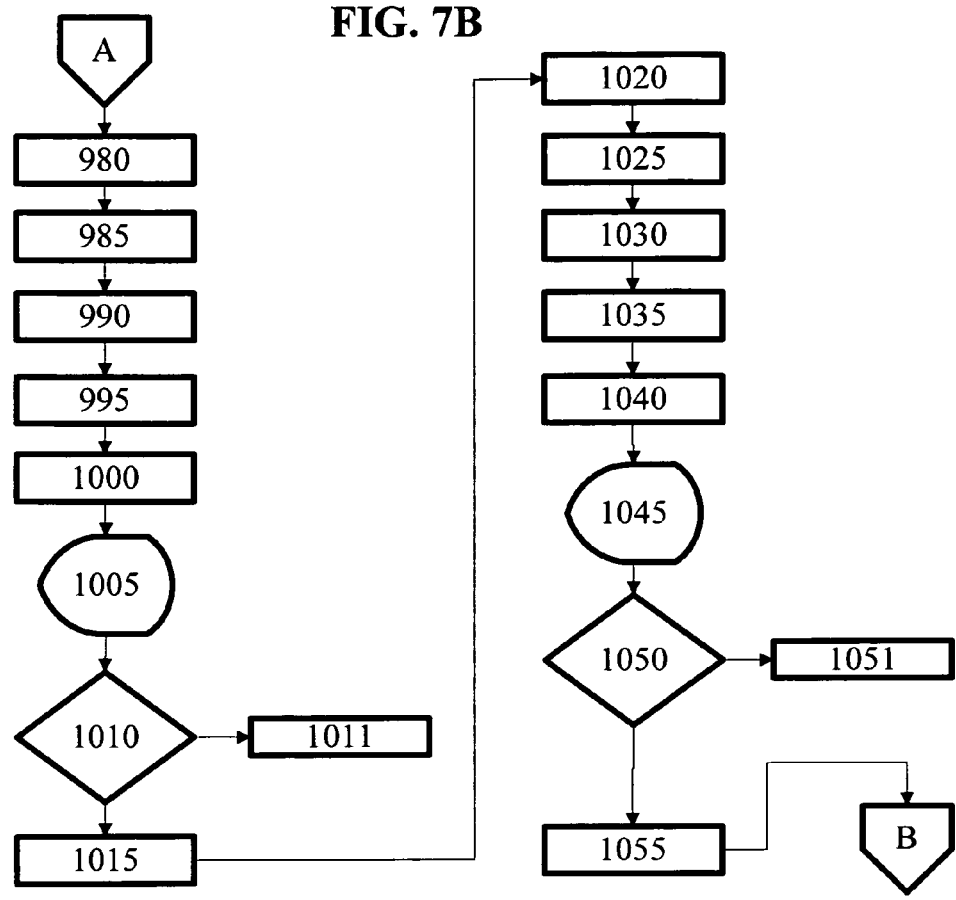
FIG. 7B illustrates a method according to another aspect of the present invention.
Figure 7C:
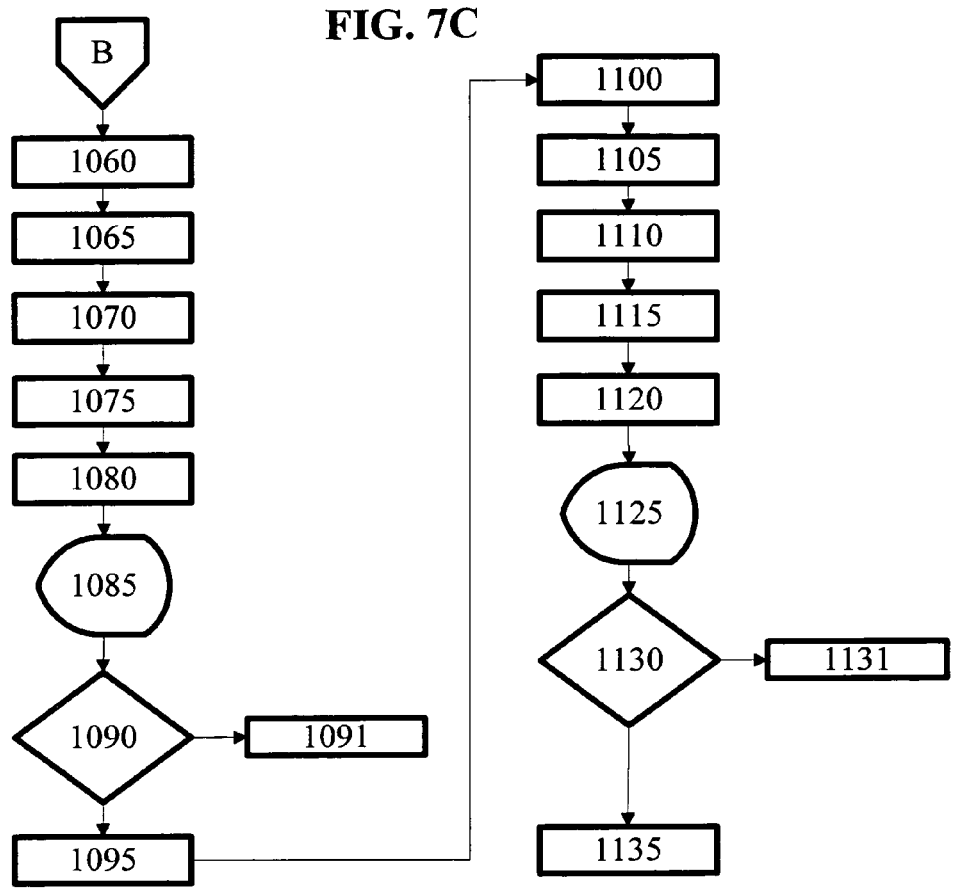
FIG. 7C illustrates a method according to another aspect of the present invention.

As shown in FIGS. 7A, 7B, and 7C, according to one aspect of the present invention a manufacturer of a host product may use systems and methods of the present invention to track the acceptability of the host product throughout the steps of its supply or distribution chain for the host product. For example, at step 900, the manufacturer may associate one or more host products with a product label 100 (as shown in FIGS. 1, 2A, and 2B) including at least two of one or more monitors, product identification elements, and authentication elements. During the association (at step 900), the manufacturer may set the limits or other data for each of the one or more monitors, product identification elements, and/or authentication elements; or, the manufacturer may use one or more monitors, product identification elements, and/or authentication elements with pre-set limits and/or data as appropriate for the particular host product.

At step 904, before the manufacturer is ready to release the product for distribution through its supply chain, an image capture and communication device may analyze a product label 100 (as shown in FIGS. 1, 2A, and 2B) of a host product at the host product's site of manufacture. Based on its analysis, for example, by scanning for visual or electronic signals indicative of one or more authentication elements, monitors, and/or identification elements present on product label 100, the image capture and communication device determines a type and one or more features for each of the one or more authentication elements, monitors, and/or identification elements, as shown at step 905.

At step 910, the image capture and communication device may access the one or more host servers 190 (as shown in FIG. 1). The image capture and communication device may accomplish such access by connecting to host servers 190 through network 185 (as shown in FIG. 1) and/or cellular network 180 (as shown in FIG. 1). In other aspects, the image capture and communication device may connect to host servers 190 through a direct satellite link. Once the image capture and communication device is either directly or indirectly connected to the host server, the image capture and communication device may transmit the type and features for each of one or more authentication elements, monitors, and/or identification elements present on product label 100, as shown at step 915. The image capture and communication device may transmit the type and features to the host servers 190 (as shown in FIG. 1) via short message service (SMS) text message, TCP/IP messaging, email, FTP, PIN email, and/or instant message. The image capture and communication device may receive an acceptability report from host servers 190 (as shown in FIG. 1) based on the type and features for each of one or more authentication elements, monitors, and/or identification elements present on product label 100, as shown at step 920. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 925, according to one aspect of the present invention, the image capture and communication device may output the acceptability report. For example, image capture and communication devices 170, 160, and/or 110 may output a text-based and/or graphical-based acceptability report on display devices such as a LCD display, LED display, or CRT display. In addition, an audible report may be output in lieu of—or in addition to—the graphically displayed report. At step 930, based on the outputted acceptability report, either the user of the image capture and communication device—or the device itself—may determine whether the host product is acceptable for use. For example, the acceptability report may actually state "it is not acceptable for distribution" or "it is acceptable distribution" or provide certain data for interpretation by its user or the device/host servers itself/themselves. At step 931, if the host product is not acceptable for use, it may not be shipped out. In a further aspect, the acceptability report may include instructions transmitted or generated by the manufacturer about what the user should do with an unacceptable product. If the product is acceptable for use, at step 935, the host product is released to a supply chain intermediary user, such as a distributor or wholesaler.

At step 940, the clinic and/or delivery driver may analyze the inbound product label 100 (as shown in FIGS. 1, 2A, and 2B) of the host product at the clinic. Based on its analysis, the image capture and communication device determines a type and one or more features for each of the one or more authentication elements, monitors, and/or identification elements, as shown at step 945.

At step 950, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 955. The image capture and communication device may receive an acceptability report from host servers 190 (as shown in FIG. 1) based on the type and features for each of one or more authentication elements, monitors, and/or identification elements present on product label 100, as shown at step 960. In addition, the acceptability report may also take into account historical information about the host product, including the data collected at the site of manufacture. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 965, the image capture and communication device may output the acceptability report. At step 970, based on the outputted acceptability report, either the user of the image capture and communication device—or the device itself— may determine whether the host product is acceptable for use. At step 971, if the host product is not acceptable for use, it may cease the supply chain process (for example, not further distribute the host product) and return it to the manufacturer. In a further aspect, the acceptability report may include instructions transmitted or generated by the manufacturer about what the supply chain intermediary user should do with an unacceptable product. If the product is acceptable for use, at step 975, the host product may be stored until such time as the supply chain intermediary user decides to release the host product to an end-user.

At step 980, the supply chain intermediary user may analyze the product label 100 (as shown in FIGS. 1, 2A, and 2B) of the stored host product. Based on its analysis, the image capture and communication device determines a type and one or more features for each of the one or more authentication elements, monitors, and/or identification elements, as shown at step 985.

At step 990, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 995. The image capture and communication device may receive an acceptability report from host servers 190 (as shown in FIG. 1) based on the type and features for each of one or more authentication elements, monitors, and/or identification elements present on product label 100, as shown at step 1000. In addition, the acceptability report may also take into account historical information about the host product, including the data collected at the site of manufacture and inbound at the supply chain intermediary user. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through an cellular network 180 (as shown in FIG. 1) or network 185 (as shown in FIG. 1). In such aspects, host servers 190 (as shown in FIG. 1) post the acceptability report to the website available at the URL.

At step 1005, the image capture and communication device may output the acceptability report. At step 1010, based on the outputted acceptability report, either the user of the image capture and communication device—or the device itself— may determine whether the host product is acceptable for use. At step 1011, if the host product is not acceptable for use, it may not be distributed to an end-user and is returned to the manufacturer. In a further aspect, the acceptability report may include instructions transmitted or generated by the manufacturer about what the supply chain intermediary user should do with an unacceptable product. If the product is acceptable for use, at step 1015, the host product may be distributed to an end-user.

At step 1020, the end-user may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 1025.

At step 1030, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 1035. The image capture and communication device may receive an acceptability report from host servers 190 (as shown in FIG. 1) based on the type and features for each of one or more authentication elements, monitors, and/or identification elements present on product label 100, as shown at step 1040. In addition, the acceptability report may also take into account historical information about the host product, including the data collected at the site of manufacture and inbound and outbound at the supply chain intermediary user's location. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 1045, the image capture and communication device may output the acceptability report. At step 1050, based on the outputted acceptability report, either the user of the image capture and communication device—or the device itself— may determine whether the host product is acceptable for use. At step 1051, if the host product is not acceptable for use, it may not be used or caused to be used by the end-user and is returned to the manufacturer directly or indirectly through the supply chain intermediary user. In a further aspect, the acceptability report may include instructions transmitted or generated by the manufacturer about what the end-user should do with an unacceptable product. If the product is acceptable for use, at step 1055, the host product may be used—or caused to be used—by the end-user.

At step 1060, the end-user may decide to return the host product to the supply chain intermediary user or the manufacturer. On the host products return to the supply chain intermediary user, the supply chain intermediary user may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 1065.

At step 1070, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 1075. The image capture and communication device may receive an acceptability report from host servers 190 (as shown in FIG. 1) based on the type and features for each of one or more authentication elements, monitors, and/or identification elements present on product label 100, as shown at step 1080. In addition, the acceptability report may also take into account historical information about the host product, including the data collected at the site of manufacture, inbound and outbound at the supply chain intermediary user's location, and at the end-user's location or place it used the host product. In a further aspect, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 1085, the image capture and communication device may output the acceptability report. At step 1090, based on the outputted acceptability report, either the user of the image capture and communication device—or the device itself—may determine whether the host product is acceptable for use. At step 1091, if the host product is not acceptable for use, it may not be re-used and thus cannot be redistributed by the clinic or manufacturer and may be returned to the manufacturer for destruction. In a further aspect, the acceptability report may include instructions transmitted or generated by the manufacturer about what the supply chain intermediary user should do with an unacceptable product. If the product is acceptable for use, at step 1095, the host product may be returned to the manufacturer for restocking and/or repackaging. In a further aspect, the acceptability report may include instructions transmitted or generated by the manufacturer about what the supply chain intermediary user should do with an acceptable product.

At step 1100, on the host product's return, the manufacturer may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 1105.

At step 1110, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 1115. The image capture and communication device may receive an acceptability report from host servers 190 (as shown in FIG. 1) based on the type and features for each of one or more authentication elements, monitors, and/or identification elements present on product label 100, as shown at step 1120. In addition, the acceptability report may also take into account historical information about the host product, including the data collected at the site of manufacture, inbound and outbound at the supply chain intermediary user's location, and at the end-user location or place the end-user used the host product. In a further aspect, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further aspects, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such aspects, host servers 190 (as shown in FIG. 1) post the acceptability report to the website available at the URL.

At step 1125, the image capture and communication device may output the acceptability report. At step 1130, based on the outputted acceptability report, either the user of the image capture and communication device—or the device itself—may determine whether the host product is acceptable for use. At step 1131, if the host product is not acceptable for use, it may not be re-stocked or repackaged and may be sent for destruction. In a further aspect, the acceptability report may include instructions transmitted or generated by the manufacturer about what the manufacturer should do with an unacceptable product. If the product is acceptable for use, at step 1135, the host product may be restocked, repackaged, and/or re-issued to a supply chain intermediary user and/or end-user.

In steps 900-1135, the one or more image capture and communication devices may be the same image capture and communication devices, different image capture and communication devices, or the same device for some steps and different devices for other steps.

Although illustrative embodiments have been shown and described herein in detail, it should be noted and will be appreciated by those skilled in the art that there may be numerous variations and other embodiments that may be equivalent to those explicitly shown and described. For example, the scope of the present invention is not necessarily limited in all cases to execution of the aforementioned steps in the order discussed. Unless otherwise specifically stated, terms and expressions have been used herein as terms of description, not of limitation. Accordingly, the invention is not to be limited by the specific illustrated and described embodiments (or the terms or expressions used to describe them) but only by the scope of claims.

What is claimed is:

1. A method for determining the acceptability of a variety of host products having labels with different types of environmental monitors, the different types of environmental monitors having different types of features, each of the labels having one or more types of environmental monitor and one or more authentication elements or identification elements, the method comprising:
   (a) capturing an image with an image capture and communication device of a product label for a host product, the product label comprising one or more environmental monitors, the product label also comprising one or more authentication elements or one or more identification elements;
   (b) determining by the image capture and communication device a type for each of the one or more environmental monitors on the product label, wherein determining the type for at least one of the environmental monitors further includes determining whether the environmental monitor contains a color reference area;
   (c) based on the respective determined types of each of the one or more environmental monitors on the product label, analyzing image features of the one or more environmental monitors, the different types of environmental monitors having different image features which are analyzed using different image analysis techniques selected based on the respective type and features of the environmental monitor,
   wherein analyzing image features of the one or more environmental monitors includes, conditioned on the environmental monitor containing a color reference area, comparing an active area of the environmental monitor with the color reference area, and conditioned on the environmental monitor not containing a color reference area, analyzing the image of the environmental monitor to measure the active area without comparing it to a color reference area,
   (d) obtaining environmental monitoring data from each of the one or more environmental monitors on the product label using the respective image analysis techniques for the environmental monitors;
   (e) transmitting by the image capture and communication device to a host server the environmental monitoring data from the one or more environmental monitors and data based on the one or more authentication elements or one or more identification elements;
   (f) receiving by the image capture and communication device from the host server an acceptability report based on the environmental monitoring data and the data based on the one or more authentication elements or one or more identification elements; and
   (g) outputting by the image capture and communication device the acceptability report.

2. The method of claim 1, wherein the one or more environmental monitors, one or more authentication elements, and one or more identification elements include one or more RFID devices.

3. The method of claim 2, wherein the one or more identification elements includes an RFID device or barcode.

4. The method of claim 1, wherein the one or more authentication elements includes an area printed with special ink.

5. The method of claim 2, further comprising: transmitting an interrogation signal to the RFID device.

6. The method of claim 1, wherein the image capture and communication device is a smartphone having a camera.

7. The method of claim 1, wherein the image capture and communication device is a computer and a camera.

8. The method of claim 1, wherein the image capture and communication device includes a barcode scanner.

9. The method of claim 1, wherein the image capture and communication device further comprises a plurality of image capture and communication devices.

10. The method of claim 1, wherein the host server further comprises one or more computers having one or more memories and one or more non-transitory computer readable storage media distributed over more than one physical location.

11. The method of claim 1, wherein the product label further comprises a plurality of product labels.

12. The method of claim 1, wherein the host product further comprises a plurality of host products.

13. An image capture and communication device comprising:
   (a) one or more memories each having at least one region for storing computer executable program code; and
   (b) a processor for executing the program code stored in the one or more memories, wherein the program code comprises:
      (b)(i) code to analyze a product label for a host product, the product label comprising one or more environmental monitors having different types of features, the product label further comprising one or more authentication elements or one or more identification elements;
      (b)(ii) code to determine a type for each of the one or more environmental monitors including code to determine whether an environmental monitor contains a color reference area;
      (b)(iii) code to analyze image features of each of the one or more environmental monitors based on their respective types, the code using different image analysis techniques selected based on the respective type and features of the one or more environmental monitors, the code to analyze image features including code that, conditioned on the environmental monitor containing a color reference area compares an active area of the environmental monitor with the color reference area, and conditioned on the environmental monitor not containing a color reference area, analyzes the environmental monitor by measure the active area without comparing it to a color reference area;
      (b)(iv) code to transmit to a host server the environmental monitoring data for the one or more environmental monitors and data based on and one or more authentication elements or one or more identification elements;
      (b)(v) code to receive from the host server an acceptability report based on the environmental monitoring data and data from the one or more authentication elements or one or more identification elements; and
      (b)(vi) code to output the acceptability report.

14. The method of claim 1 wherein the one or more environmental monitors include a cumulative time-temperature indicator.

15. The method of claim 1 wherein the plurality of environmental monitors includes a freeze indicator.

16. The method of claim 1 wherein the one or more environmental monitors include one or more threshold indicators configured to indicate previous exposure to a temperature above a preset limit.

17. The method of claim 1 wherein the one or more environmental monitors include an environmental history monitor.

18. The image capture and communication device of claim 13 wherein the one or more environmental monitors include an environmental history monitor.

19. The method of claim 1, further comprising:
(a) analyzing by an image capture and communication device a second product label for a second host product, the second product label comprising one or more second environmental monitors and comprising one or more second authentication elements or one or more second identification elements, at least one of second environmental monitors being of a different type than the one or more environmental monitors for the host product;
(b) determining by the image capture and communication device a second type for each of the one or more second environmental monitors on the second product label for the second host product;
(c) based on the respective second types of each the one or more second environmental monitors on the second product label for the second host product, determining second features of the one or more second environmental monitors
(d) transmitting by the image capture and communication device to a host server second data based on the respective second type and second features for each of the one or more second environmental monitors and one or more second authentication elements or one or more second identification elements;
(e) receiving by the image capture and communication device from the host server a second acceptability report based on the second data for the one or more second environmental monitors and one or more second authentication elements or one or more second identification elements; and
(f) outputting by the image capture and communication device the second acceptability report.

20. The method of claim 1 wherein the one or more environmental monitors include a heat exposure indicators.

21. The method of claim 1, wherein the features of the one or more environmental monitors include the color of an active zone of the one or more environmental monitors.

22. The method of claim 21, wherein the features of the one or more environmental monitors include the color of a reference zone of the one or more environmental monitors.

23. The method of claim 1, wherein the acceptability report is conditioned on whether the data from the features of the one or more environmental monitors indicates the host product was exposed to environmental conditions outside set limits for the host product.

24. The device of claim 13, wherein the one or more authentication elements includes a symbol.

25. The device of claim 13, wherein the one or more environmental monitors, one or more authentication elements, and one or more identification elements include one or more RFID devices.

26. The device of claim 13, wherein the one or more identification elements includes an RFID device or barcode.

27. The device of claim 13, wherein the one or more environmental monitors include a cumulative time-temperature indicator.

28. The device of claim 13, wherein the one or more environmental monitors include a freeze indicator.

29. The device of claim 13, wherein the one or more environmental monitors include a threshold indicator configured to indicate previous exposure to a temperature above a preset limit.

30. The device of claim 13, wherein the code further comprises:
(a) code to analyze a second product label for a second host product, the second product label comprising one or more second environmental monitors and comprising one or more second authentication elements or one or more second identification elements, at least one of second environmental monitors being of a different type than the one or more environmental monitors for the host product;
(b) code to determine a second type for each of the one or more second environmental monitors on the second product label for the second host product;
(c) code to determine one or more second features of each of the one or more second environmental monitors based on their respective second types;
(d) code to transmit to a host server second data based on the respective second type and second features for each of the one or more second environmental monitors and one or more second authentication elements or one or more second identification elements;
(e) code to receive from the host server a second acceptability report based on the second data for the one or more second environmental monitors and one or more second authentication elements or one or more second identification elements; and
(f) code to output the second acceptability report.

31. The method of claim 1, wherein the label includes a plurality of environmental monitors of different types, and wherein different image analysis techniques are used to analyze the environmental monitors on the same label.

32. The device of claim 13, wherein the label includes a plurality of environmental monitors of different types, and wherein the code to analyze the image features includes code to analyze each of the different types of environmental monitors found on the same label.

* * * * *